(12) United States Patent
Chewter et al.

(10) Patent No.: US 7,932,427 B2
(45) Date of Patent: Apr. 26, 2011

(54) PROCESS FOR THE PREPARATION OF PROPYLENE AND INDUSTRIAL PLANT THEREOF

(75) Inventors: Leslie Andrew Chewter, Amsterdam (NL); Michiel Johannes Franciscus Maria Verhaak, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 276 days.

(21) Appl. No.: 12/301,177

(22) PCT Filed: May 16, 2007

(86) PCT No.: PCT/EP2007/054739
§ 371 (c)(1), (2), (4) Date: Nov. 17, 2008

(87) PCT Pub. No.: WO2007/135043
PCT Pub. Date: Nov. 29, 2007

(65) Prior Publication Data
US 2009/0259087 A1    Oct. 15, 2009

(30) Foreign Application Priority Data
May 19, 2006 (EP) .................................. 06114272

(51) Int. Cl.
*C07C 4/06* (2006.01)
(52) U.S. Cl. .......................... 585/651; 585/650; 585/653
(58) Field of Classification Search .................. None
See application file for complete search history.

(56) References Cited

U.S. PATENT DOCUMENTS

| 679,851 | A | 8/1901 | Leckband | |
| 4,076,842 | A | 2/1978 | Plank et al. | 423/328 |
| 4,197,185 | A | 4/1980 | Le Page et al. | 208/71 |
| 4,397,827 | A | 8/1983 | Chu | 423/326 |
| 4,544,792 | A | 10/1985 | Smith et al. | 545/533 |
| 4,556,477 | A | 12/1985 | Dwyer | 208/111 |
| 4,590,320 | A | 5/1986 | Sapre | 585/324 |
| 4,626,415 | A | 12/1986 | Tabak | 422/190 |
| 4,684,757 | A | 8/1987 | Avidan et al. | 585/331 |
| 6,307,117 | B1 | 10/2001 | Tsunoda et al. | 585/651 |
| 6,339,181 | B1 | 1/2002 | Chen et al. | 585/653 |
| 6,517,807 | B2* | 2/2003 | Verduijn et al. | 423/709 |
| 6,656,345 | B1* | 12/2003 | Chen et al. | 208/120.01 |
| 6,858,129 | B2* | 2/2005 | Mohr et al. | 208/120.01 |

(Continued)

FOREIGN PATENT DOCUMENTS
DE    10043644    3/2002
(Continued)

OTHER PUBLICATIONS
Meier, et al: "Atlas of Zeolite Structure Types Passage", Atlas of Zeolite Framework Types, 2001, pp. 9-20.

*Primary Examiner* — Tam M Nguyen

(57) ABSTRACT

The present invention provides a process for the preparation of propylene from a hydrocarbon feed containing one or more $C_5$ and/or $C_6$ cycloalkanes, wherein the hydrocarbon feed containing one or more $C_5$ and/or $C_6$ cycloalkanes is contacted under cracking conditions with a one-dimensional zeolite having 10-membered ring channels and a silica to alumina ratio in the range from 1 to 500 wherein at least 50% w/w of the total amount of zeolite used is zeolite in the hydrogen form.

10 Claims, 3 Drawing Sheets

U.S. PATENT DOCUMENTS

Figure 1:
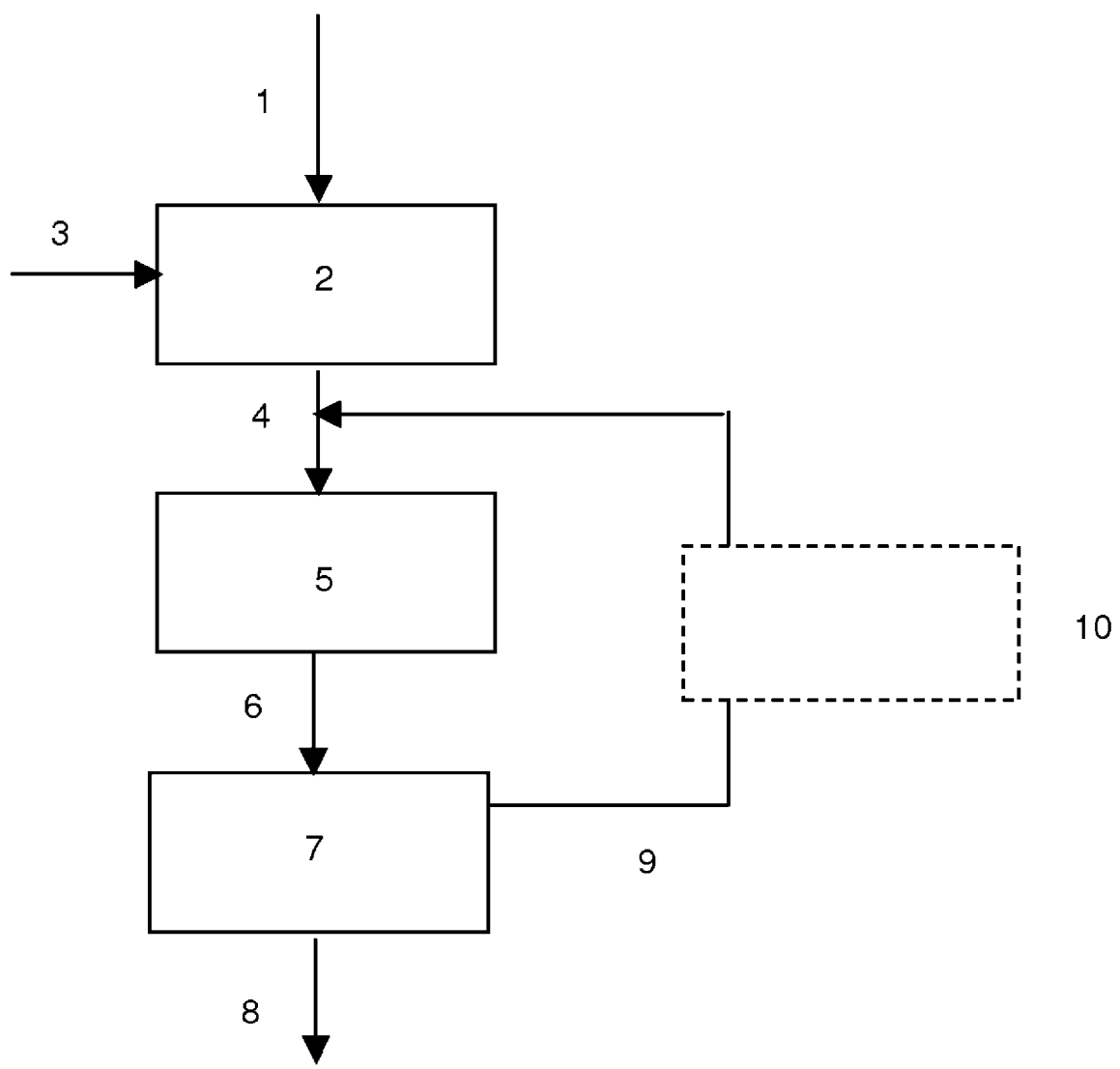

| | | |
|---|---|---|
| 7,112,307 B2 * | 9/2006 | Abrevaya et al. ............. 422/142 |
| 7,314,964 B2 * | 1/2008 | Abrevaya et al. ............. 585/651 |
| 2002/0063082 A1 | 5/2002 | Touvelle et al. ............. 208/134 |
| 2003/0078463 A1 | 4/2003 | Martens et al. ............. 585/638 |
| 2003/0125598 A1 | 7/2003 | Chisholm et al. ............. 585/640 |
| 2003/0181777 A1 | 9/2003 | Powers et al. ............. 585/648 |
| 2004/0015028 A1 | 1/2004 | Brown et al. ............. 585/520 |
| 2005/0070422 A1 * | 3/2005 | Chen et al. ............. 502/64 |
| 2005/0130832 A1 * | 6/2005 | Abrevaya et al. ............. 502/4 |

FOREIGN PATENT DOCUMENTS

| | | |
|---|---|---|
| EP | 109059 | 5/1984 |
| EP | 485145 | 5/1992 |
| EP | 788838 | 8/1997 |
| EP | 921181 | 6/1999 |
| GB | 663901 | 12/1951 |
| WO | WO9957085 | 11/1999 |
| WO | WO9957226 | 11/1999 |
| WO | WO0026163 | 5/2000 |
| WO | WO0123500 | 4/2001 |
| WO | WO0129152 | 4/2001 |
| WO | WO0134730 | 5/2001 |
| WO | WO0181280 | 11/2001 |
| WO | WO0190279 | 11/2001 |
| WO | WO0210098 | 2/2002 |
| WO | WO03020667 | 3/2003 |
| WO | WO2004018392 | 3/2004 |
| WO | WO2005016856 | 2/2005 |
| WO | WO2005028594 | 3/2005 |

* cited by examiner

PROCESS FOR THE PREPARATION OF PROPYLENE AND INDUSTRIAL PLANT THEREOF

PRIORITY CLAIM

The present application claims priority to European Patent Application 06114272.5 filed 19 May 2006.

TECHNICAL FIELD OF THE INVENTION

This invention relates to a process for the preparation of propylene from a hydrocarbon feed and an industrial set-up therefore.

BACKGROUND OF THE INVENTION

Processes for the preparation of propylene from a hydrocarbon feed are well known in the art.

The processing of hydrocarbon feeds containing $C_5$ and/or $C_6$ cycloalkanes, however, is found to be difficult. For example, in their presentation on PROPYLUR technology H. Boelt et al. indicated that paraffins, cycloalkanes, cycloalkenes and aromatics can be contained in the feedstock and pass a reactor with nearly no conversion. (see H. Boelt et al. "Recent developments in propylene technologies, part II: PROPYLUR technology, Linde European Olefin Seminar, Penha Longha (Portugal), November 2001).

In EP-A-0788838 the catalytic conversion of a raw material naphtha feed is described. In the examples raw material naphtha was converted with several ZSM-5 type zeolites, having silica to alumina ratio's ranging from about 30 to about 126. In order to obtain high yields of ethylene and propylene the use of a group Ib metal promotor such as silver was found essential. Although, in passing other zeolites such as ZSM-23 and ZSM-35 were mentioned, the use of such zeolites was not actually disclosed. The only zeolite used in the examples was ZSM-5.

In U.S. Pat. No. 6,307,117 the necessity of a group Ib metal promotor such as silver for a high yield conversion of a hydrocarbon feed to ethylene and propylene was confirmed. It was furthermore found necessary that the zeolites had a silica to alumina ratio in the range from 200 to 5000. Although, in passing other zeolites such as ZSM-23 and ZSM-35 were mentioned, the use of such zeolites was not actually disclosed. The only zeolite used in the examples was ZSM-5.

In example 10 of U.S. Pat. No. 6,307,117 a cyclopentane feed was cracked into smaller components over a ZSM-5 catalyst having a silica to alumina ratio of 300. The product included propylene and butylene in a weight ratio of propylene to butylene of about 1.6.

U.S. Pat. No. 6,339,181, describes a process for the preparation of propylene from a hydrocarbon feed stream containing $C_5$ and $C_6$ components. It is mentioned that cycloparaffins can be present in the feed, however, the patent only discloses conversion of olefins. Furthermore, although in passing other zeolites such as ZSM-23 and ZSM-35 were mentioned, the use of such zeolites was not actually disclosed. The only zeolite used in the examples was ZSM-5. The examples only disclose conversion of feed streams containing paraffins and olefins but no cycloparaffins. In the non-comparative examples the $C_5/C_6$ cut was only contacted with a SAPO-11 catalyst. The product included propylene and butylene in a propylene to butylene weight ratio in the range from about 1.4 to about 3.8.

US-A-2002/0063082 describes a method for converting a naphtha feed having naphthene ring-containing compounds (s.i.c) by first contacting the naphtha feed with a ring opening catalyst, comprising e.g. Ru, Rh, Ir, or Pt to form a ring-opened product, whereafter this ring opened product can be catalytically cracked by a medium pore crystalline silicate zeolite catalyst. It would be useful to have a process wherein such a naphtha feed can be directly converted into propylene.

It would be desirable to have a process that would be able to convert a hydrocarbon feedstock containing $C_5$ and/or $C_6$ cycloalkanes in an economically viable manner in high selectivity into propylene with little co-production of undesirable butene-byproducts.

SUMMARY OF THE INVENTION

It has now been surprisingly found that a $C_5$ and/or $C_6$ cycloalkane containing hydrocarbon feed can be converted to propylene with a high selectivity, little co-production of undesirable butene-byproducts and without the necessity for a Ib metal promoter, when a one-dimensional zeolite having 10-membered ring channels and a silica to alumina ratio in the range from 1 to 500, is used.

Accordingly, the present invention provides a process for the preparation of propylene from a hydrocarbon feed containing one or more $C_5$ and/or $C_6$ cycloalkanes, wherein the hydrocarbon feed containing one or more $C_5$ and/or $C_6$ cycloalkanes is contacted under cracking conditions with a one-dimensional zeolite having 10-membered ring channels and a silica to alumina ratio in the range from 1 to 500.

The invention further provides several industrial set-ups for such a process.

BREIF DESCRIPTION OF THE DRAWINGS

The invention has been illustrated by the following figures.

FIG. 1: Example of a first industrial set-up and process according to the invention FIG. 2: Example of a second industrial set-up and process according to the invention FIG. 3: Example of a third industrial set-up and process according to the invention

DETAILED DESCRIPTION OF THE INVENTION

The hydrocarbon feed containing one or more $C_5$ and/or $C_6$ cycloalkanes can comprise a wide range of $C_5$ and/or $C_6$ cycloalkanes. By a $C_5$ and/or $C_6$ cycloalkane is understood a cycloalkane having 5 respectively 6 carbon atoms or a mixture of such cycloalkanes.

Such a cycloalkane can have for example 4, 5 or 6 carbon atoms in the ring. If the cycloalkane has 4 or 5 carbon atoms in the ring, it can be substituted with one or more alkyl groups, preferably methyl and/or ethyl groups. That is, the cycloalkane can for example be a cyclobutane derivative, cyclopentane or derivative thereof or cyclohexane.

The $C_5$ and/or $C_6$ cycloalkane can further comprise other atoms than carbon and hydrogen atoms, such as for example oxygen and sulphur atoms. Preferably, however, the $C_5$ and/or $C_6$ cycloalkane only contains carbon atoms and hydrogen atoms. The $C_5$ and/or $C_6$ cycloalkane is preferably a cycloalkane having 5 carbon atoms in the ring, preferably non-substituted or substituted with one methyl group. Examples of $C_5$ and/or $C_6$ cycloalkanes include cyclopentane, methyl-cyclopentane, ethyl-cyclobutane, dimethyl-cyclobutane and cyclohexane, of which the cyclopentanes and cyclohexane, especially cyclopentane, methyl-cyclopentane and cyclohexane, are preferred.

The hydrocarbon feed can comprise just one cycloalkane or a mixture of cycloalkanes. In a preferred embodiment the hydrocarbon feed contains a mixture of $C_5$ and/or $C_6$ cycloalkanes, preferably a mixture of cyclopentane, methyl-cyclopentane and cyclohexane.

The hydrocarbon feed can comprise in the range from 0.1 to 100% w/w of $C_5$ and/or $C_6$ cycloalkanes. Preferably the hydrocarbon feed comprises at least 0.5% w/w of $C_5$ and/or $C_6$ cycloalkanes, more preferably at least 1% w/w of $C_5$ and/or $C_6$ cycloalkanes.

In one embodiment the $C_5$ and/or $C_6$ cycloalkanes form only a limited part of the hydrocarbon feed, and the hydrocarbon feed preferably comprises at most 80% w/w of $C_5$ and/or $C_6$ cycloalkanes, more preferably at most 70% w/w, and more preferably at most 50% w/w of $C_5$ and/or $C_6$ cycloalkanes. Most preferably such hydrocarbon feed comprises from 1 to 40% w/w of $C_5$ and/or $C_6$ cycloalkanes.

In another embodiment the hydrocarbon feed is derived from a source generating mainly $C_5$ and/or $C_6$ cycloalkanes, and the hydrocarbon feed preferably comprises in the range from 50 to 100% w/w, and most preferably from 80 to 100% w/w of $C_5$ and/or $C_6$ cycloalkanes.

In addition to the $C_5$ and/or $C_6$ cycloalkanes, the hydrocarbon feed can contain other hydrocarbons. For example, the hydrocarbon feed can contain in addition other linear, branched or cyclic hydrocarbons. Such linear, branched or cyclic hydrocarbons can be saturated or unsaturated. Such linear, branched or cyclic hydrocarbons can further comprise other atoms than carbon and hydrogen atoms, such as for example oxygen or sulphur atoms. Preferably, however, the hydrocarbon feed comprises hydrocarbons merely containing carbon atoms and hydrogen atoms. Examples of hydrocarbons that can be present in the hydrocarbon feed in addition to the $C_5$ and/or $C_6$ cycloalkanes include further cycloalkanes, such as for example cycloheptane, methylcyclohexane, dimethylcyclopentane, ethylcyclopentane, cyclobutane; cycloalkenes, such as for example, cyclopentene, methylcyclobutene, cyclohexene, methylcyclopentene, cycloheptene, methylcyclohexene, dimethylcyclopentene, ethylcyclopentene; cycloalkadienes, such as for example cyclopentadiene, cyclohexadiene, methylcyclopentadiene, cycloheptadiene, methylcyclohexadiene, dimethylcyclopentadiene, ethylcyclopentadiene; linear and branched alkanes, such as for example n-butane, methyl-propane (isobutane), n-pentane, methyl-butane, dimethyl-propane, n-hexane, methyl-pentane, dimethylbutane, n-heptane, methyl-hexane, dimethyl-pentane, ethyl-pentane, octanes, nonanes decanes etc.; linear and branched alkenes and alkadienes, such as for example n-butene, methyl-propene (isobutene), n-pentene, methyl-butene (e.g. 2-methyl-2-butene), dimethyl-propene, n-hexene, methyl-pentene, dimethylbutene, n-heptene, methyl-hexene, dimethyl-pentene, ethyl-pentene, octenes, nonenes decenes, butadiene, pentadienes, methyl-butadiene, hexadienes, methyl-pentadienes, heptadienes, methyl-hexadienes etc.

In a preferred embodiment feeds with a limited amount of alkadienes, for example amounts smaller than 1%, are used.

Preferably the hydrocarbon feed is a $C_5$-$C_6$ hydrocarbon feed. By a $C_5$-$C_6$ hydrocarbon feed is understood a hydrocarbon feed containing mainly compounds having 5 or 6 carbon atoms, that is a hydrocarbon feed containing at least 50% w/w of compounds with 5 or 6 carbon atoms. More preferably the hydrocarbon feed comprises more than 60% w/w, more preferably more than 70% w/w and most preferably more than 80% w/w of compounds having 5 or 6 carbon atoms.

Such a $C_5$-$C_6$ hydrocarbon feed can for example contain linear and/or branched $C_5$ and/or $C_6$ paraffins (alkanes); linear and/or branched $C_5$ and/or $C_6$ olefins (alkenes) and/or diolefins (alkadienes); and/or $C_5$ and/or $C_6$ cycloparaffins, cycloolefins (cyclic alkenes) and/or cyclo-diolefins (cyclic alkadienes).

Preferably the hydrocarbon feed containing $C_5$ and/or $C_6$ cycloalkanes is a hydrocarbon feed boiling in the range from 1° C. to 150° C., more preferably in the range from 10° C. to 110° C., and most preferably in the range from 20° C. to 90° C.

Examples of suitable hydrocarbon feeds to the process include
   a $C_5$-hydrocarbon stream obtained from cracking and full hydrogenation of a dicyclopentadiene stream. Such a dicyclopentadiene stream derived $C_5$-hydrocarbon stream generally contains more than 50% w/w of cyclopentane.
   a $C_5$-hydrocarbon stream obtained after distillation from pyrolysis gasoline as further described below. Such a $C_5$-hydrocarbon stream (i.e. a stream containing hydrocarbons having 5 carbon atoms) can be partly or fully hydrogenated before use in the process of the invention;
   a $C_6$-hydrocarbon stream obtained after distillation from pyrolysis gasoline. Preferably such a $C_6$-hydrocarbon stream (i.e. a stream containing hydrocarbons having 6 carbon atoms) is fully hydrogenated and benzene is extracted therefrom, before use in the process of the invention;
   a (part of a) $C_6$-hydrocarbon stream obtained from a reformer;

Especially preferred hydrocarbon feeds are the, optionally hydrogenated, $C_5$ and/or $C_6$ distillation streams of a pyrolysis gasoline that is produced in a steam cracker. In a steam cracker feeds such as for example naphtha (boiling e.g. between about 25° C. and about 180° C., preferably boiling between about 30° C. and about 160° C., more preferably boiling between about 35° C. and about 150° C.), gasoil (boiling e.g. between about 120° C. and about 370° C., preferably boiling between about 150° C. and about 300° C., more preferably boiling between about 180° C. and about 250° C.) and hydrowax or vacuum gasoil (boiling e.g. between about 200° C. and about 700° C., more preferably between about 250° C. and about 600° C.) are converted into lighter products.

The product stream can be distilled into several fractions. By a pyrolysis gasoline is understood a distillation fraction, boiling between $C_5$-205° C., preferably between 25° C. and 180° C., obtained after distillation of the product stream of such a steam cracker, such as for example illustrated in the Petroleum Handbook, 6th edition, compiled by the staff of the Royal Dutch/shell Group of Companies, published by Elsevier (1983), page 309.

The pyrolysis gasoline can be split into several product streams by for example distillation, extraction or other separation methods. Preferably a so-called "$C_5$-cut" (boiling between about 25° C. and 55° C.) and a so-called "$C_6$-cut" (boiling between about 55° C. and 88° C.) are separated from the pyrolysis gasoline. These "$C_5$-cut" and "$C_6$-cut" can be partially or fully hydrogenated, and preferably the "$C_6$-cut" is furthermore processed in a benzene extraction unit to remove benzene from the product stream.

Preferably, the "$C_5$-cut" is, partially or fully, hydrogenated. By full hydrogenation is understood hydrogenation of all olefins (mono- and di-) under hydrogenation conditions to such an extent that the resultant concentration of olefins is below 0.5% w/w based on the total composition. By partial hydrogenation is understood a hydrogenation under hydrogenation conditions wherein all less than all olefins are hydrogenated, i.e. wherein the resultant concentration of olefins is 0.5% w/w or more. Preferably the partial hydrogenation is carried out such that more than 90% w/w, preferably more than 95% w/w and most preferably 100% w/w of the di-olefins present are converted into mono-olefins or, preferably only to limited extent, paraffins, whilst hydrogenation of the mono-olefins is kept as low as possible. Most preferably the $C_5$ stream is hydrogenated to such an extent that the di-olefin concentration after the hydrogenation step is below 0.5% w/w and the mono-olefin concentration after the hydrogenation step is above 0.5% w/w based on the total composition. A non-hydrogenated "$C_5$-cut" can contain for example in the range from 40 to 80% w/w di-olefins, including for example 10 to 40% w/w of cyclopentadienes; in the range from 10 to 40% w/w mono-olefins, including for example 0.1 to 5% w/w of cyclopentenes; and in the range from 5 to 40% w/w of paraffins, including for example 0.1 to 5% w/w of cyclopentanes.

A partially hydrogenated "$C_5$-cut" can contain for example in the range from 0 to 1% w/w di-olefins; in the range from 10 to 95% w/w mono-olefins, including for example 0 to 40% w/w of cyclopentenes; and in the range from 5 to 80% w/w of paraffins, including for example 0.1 to 5% of cyclopentanes.

In addition the "$C_5$-cut" can contain certain amounts (i.e. in the range from 0.01 to 30% w/w) of $C_4$ and/or $C_6$ hydrocarbons.

Preferably a partly hydrogenated hydrowax-, naphtha- or gasoil-derived "$C_5$-cut" is used in the process according to the invention. Most preferably a partly hydrogenated hydrowax-derived "$C_5$-cut" is used.

The "$C_6$-cut" is preferably fully hydrogenated and furthermore treated in a benzene extraction unit to remove benzene from the product stream.

A fully hydrogenated "$C_6$-cut" from pyrolysis gasoline from which benzene is extracted can contain for example in the range from 20 to 90% w/w of paraffins, including for example 20 to 90% w/w, of cycloalkanes, such as cyclohexane and methylcyclopentane; and optionally up to about 10% of residual benzene.

In a further preferred embodiment a fully or partially hydrogenated "$C_5$-cut" and a fully hydrogenated and benzene extracted "$C_6$-cut" are combined and fed into the process according to the invention.

In addition the "$C_6$-cut" can contain certain amounts (for example in the range from 0.01 to 30% w/w) of $C_5$ and/or $C_7$ hydrocarbons.

It is found that unsaturated cyclic hydrocarbons, such as for example $C_5$ and/or $C_6$ cyclic alkenes or cyclic alkadienes, are difficult to convert to further products by cracking. After conversion of such $C_5$ and/or $C_6$ cyclic alkenes or cyclic alkadienes into $C_5$ and/or $C_6$ cycloalkanes, the cycloalkanes can advantageously be fed in the process of the present invention.

The present invention therefore also provides a process for the preparation of propylene from a hydrocarbon feed containing one or more $C_5$-$C_6$ cyclic alkenes and/or $C_5$-$C_6$ cyclic alkadienes, containing the steps of a) converting at least part of the $C_5$-$C_6$ cyclic alkenes and/or $C_5$-$C_6$ cyclic alkadienes into $C_5$-$C_6$ cycloalkanes; and
b) converting the $C_5$-$C_6$ cycloalkanes of step a) with a process as described herein, to yield propylene.

Step a) can be carried out in any manner known by the skilled person to be suitable for this purpose. Preferably, however, step a) is carried out by hydrogenation of the $C_5$ and/or $C_6$ cyclic alkenes and/or cyclic alkadienes. Such a hydrogenation can be carried out in any manner known by the skilled person to be suitable for this purpose. Such a hydrogenation process is for example described in the Handbook of petroleum refining processes 2nd edition by Robert A. Meyers, published by Mc Graw Hill (1997) pages 8.27 and 8.28; and in the Petroleum Handbook, 6th edition, compiled by the staff of the Royal Dutch/shell Group of Companies, published by Elsevier (1983), pages 309-311. A suitable hydrogenation process is for example further described in WO-A-2005/028594 under the section selective hydrogenation.

Hydrogenation can be accomplished by contacting the $C_5$ and/or $C_6$ cyclic alkenes and/or cyclic alkadienes with a hydrogenation catalyst in the presence of hydrogen. The hydrogenation catalyst can be any composition effective for hydrogenating unsaturated hydrocarbons. Preferably, the hydrogenation catalyst can comprises a Group VIII metal selected from the group consisting of iron, cobalt, nickel, ruthenium, rhodium, palladium, osmium, iridium, platinum and combinations of any two or more thereof. Most preferably, the hydrogenation catalyst comprises palladium. The hydrogenation can be carried out under reaction conditions known by the skilled person to be effective for hydrogenating unsaturated hydrocarbons. For practical purposes, the reaction temperature may lie in the range from about 30° C. to about 250° C., preferably from about 50° C. to about 200° C.

The hydrogenation of a $C_5$ distillation stream of a pyrolysis gasoline is preferably carried out at a temperature in the range from 50° C. to 150° C., most preferably in the range from 60° C. to 70° C. For practical purposes the total pressure can range from about 20 bar to about 60 bar, preferably from about 25 bar to about 40 bar. Preferably the hydrogen pressure is adjusted such that the partial hydrogen pressure at the outlet of the reactor is more than 15 bar. The ratio of volume of hydrogen gas to volume hydrocarbon feed preferably lies in the range from 75:1 v/v to about 300:1 v/v. The volume of hydrocarbon feed/per volume of catalyst per hour preferably lies in the range from 1 to 10, more preferably 2 to 5 liter/liter/hour.

Step a) generates a $C_5$ and/or $C_6$ cycloalkane stream which can subsequently be cracked in step b) in the presence of a zeolite as described herein.

In a preferred embodiment the hydrocarbon feed in the present invention is therefore a hydrocarbon feed containing one or more $C_5$ and/or $C_6$ cycloalkanes obtained after hydrogenation of a hydrocarbon feed containing one or more $C_5$ and/or $C_6$ cyclic alkenes and/or cyclic alkadienes, such as for example cyclopentenes, cyclohexenes, cyclopentadienes and cyclohexadienes.

The hydrocarbon feed containing one or more $C_5$ and/or $C_6$ cycloalkanes is contacted with a one-dimensional zeolite having 10-membered ring channels and a silica to alumina ratio in the range from 1 to 500.

The zeolite is a one-dimensional zeolite having 10-membered ring channels. These are understood to be zeolites having only 10-membered ring channels in one direction which are not intersected by other 8, 10 or 12-membered ring channels.

Preferably the zeolite is selected from the group of TON-type (for example ZSM-22), MTT-type (for example ZSM-23), STF-type (for example SSZ-35), SFF-type (for example SSZ-44), and EU-2/ZSM-48 zeolites.

The zeolites used in the present invention are distinct from zeolites having small pore 8-ring channels or zeolites having large pore 12-ring channels.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type zeolites are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type zeolites are more particularly described in e.g. U.S. Pat. No. 4,397,827. For purposes of the present invention, EU-2 is considered to include its isotypes, e.g., ZSM-48.

In a further preferred embodiment a zeolite of the MTT-type, such as ZSM-23, is used.

Preferably a zeolite in the hydrogen form is used, e.g., HZSM-22, HZSM-23, H-ZSM-35, HZSM-48 and preferably at least 50% w/w, more preferably at least 90% w/w, still more preferably at least 95% w/w and most preferably 100% of the total amount of zeolite used is zeolite in the hydrogen form. When the zeolites are prepared in the presence of organic cations the zeolite may be activated by heating in an inert or oxidative atmosphere to remove the organic cations, for example, by heating at a temperature over 500° C. for 1 hour or more. The hydrogen form can then be obtained by an ion exchange procedure with ammonium salts followed by another heat treatment, for example in an inert or oxidative atmosphere at a temperature over 500° C. for 1 hour or more. The latter zeolites are also referred to as being in the ammonium form.

The zeolite has a silica to alumina ratio (SAR) in the range from 1 to 500. Preferably the zeolite has a SAR in the range from 10 to 200.

The zeolite can be used as such or in combination with a so-called binder material. When used in the reaction, the zeolite as such or the zeolite in combination with a binder material, are hereafter also referred to as zeolite catalyst.

It is desirable to provide a catalyst having good mechanical strength, because in an industrial environment the catalyst is often subjected to rough handling which tends to break down the catalyst into powder-like material. The later causes problems in the processing. Preferably the zeolite is therefore incorporated in a binder material. Examples of suitable binder materials include active and inactive materials and synthetic or naturally occurring zeolites as well as inorganic materials such as clays, silica, alumina, aluminosilicate. For present purposes, inactive materials of a low acidity, such as silica, are preferred because they may prevent unwanted side reactions which may take place in case a more acidic material, such as alumina is used. Preferably the catalyst used in the process of the present invention comprises, in addition to the zeolite, 2 to 90 wt %, preferably 10 to 85 wt % of a binder material.

The process of the present invention can be carried out in a batch, continuous, semi-batch or semi-continuous manner using conventional reactor systems such as fixed bed, moving bed, fluidized bed and the like. As a reactor any reactor known to the skilled person to be suitable for catalytic cracking can be used.

Conventional catalyst regeneration techniques can be employed. The catalyst used in the process of the present invention can have any shape known to the skilled person to be suitable for this purpose, for example the catalyst can be present in the form of catalyst tablets, rings, extrudates, etc. extruded catalysts can be applied in various shapes, such as, cylinders and trilobes.

If desired, spent catalyst can be regenerated and recycled to the process of the invention.

The hydrocarbon feed is contacted with a zeolite catalyst under cracking conditions.

By cracking conditions is understood any reaction conditions known to the skilled person to be effective in cracking hydrocarbons into smaller hydrocarbons. The process can be carried out over a wide range of temperatures and pressures. Preferably, however, the hydrocarbon feed is contacted with the zeolite catalyst at a temperature in the range from 300° C. to 700° C., more preferably in the range from 400° C. to 600° C. and at an absolute pressure in the range from 1 to 5 bar.

The hydrocarbon feed may be diluted with a diluent gas. Any diluent gas known by the skilled person to be suitable for such purpose can be used. Examples of a diluent gas include argon, nitrogen and steam. For example, the oxygenate feed and/or olefinic co-feed can be diluted with steam, for example in the range from 0.01 to 10 kg steam per kg feed.

In a further embodiment, small amounts of water are added in order to improve the stability of the catalyst by reducing coke formation.

The process according to the invention can advantageously be carried out in the absence of any metals belonging to Group Ib of the periodic table. By the absence of Group Ib metals is understood that, if present, the weight percentage of Group Ib metals on total amount of the zeolite is less than 0.1% w/w, more preferably less than 0.01% w/w, even more preferably less than 50 ppmw still more preferably less than 10 ppmw and most preferably non-existent.

Preferably the process is carried out in the absence of oxygenates. By the absence of oxygenates is understood that, if present, the weight percentage of oxygenates on total amount of the hydrocarbon feed is less than 5% w/w, more preferably less than 1% w/w, even more preferably less than 0.1% w/w, still more preferably less than 0.01% w/w and most preferably non-existent.

With the process according to the invention the amount of butene-byproducts prepared is limited. As illustrated in the examples propylene to butylene weight ratios of well over 10 can be obtained.

A product stream of propylene can be separated from the reaction product by any method known to the person skilled in the art. Preferably such a separation is carried out in one or more distillation columns.

Depending on the hydrocarbon feed used, the reaction product can further contain, in addition to the propylene, several $C_{4+}$ hydrocarbons (i.e. hydrocarbons having 4 or more carbon atoms). For example, if the hydrocarbon feed contained unsaturated hydrocarbons, such as for example cyclopentene, methylcyclopentene, these may still be present in the reaction product. In addition the reaction product can contain unreacted $C_5$ and/or $C_6$ cycloalkanes. Further the reaction product can contain other $C_5$ and/or $C_6$ hydrocarbons such as linear or branched $C_5$ and/or $C_6$ alkanes and/or alkenes.

The product stream obtained after separation of the propylene can be further processed in several ways. For example, a product stream containing $C_{4+}$ compounds can be partly or fully fed into a subsequent steam cracker. If the product stream containing $C_{4+}$ compounds contains any unsaturated hydrocarbons, the stream is preferably first fully hydrogenated in a (second) hydrogenation reactor before being fed to a subsequent steam cracker.

Alternatively a product stream containing $C_{4+}$ compounds can be partly or fully recycled into the process according to the invention. Again, if the product stream containing $C_{4+}$ compounds contains any unsaturated hydrocarbons, the stream is preferably first fully hydrogenated in a (second) hydrogenation reactor before being recycled.

It can further be advantageous to split a product stream containing $C_{4+}$ compounds into a part to be fed to a steam cracker and a part to be recycled to the catalytic cracker of the process of the invention.

Especially when the product stream containing $C_{4+}$ compounds contains a substantial amount (i.e. more than 50% wt based on the total amount of $C_{4+}$ compounds) of linear and branched alkanes, it is preferred to split the product stream in a stream of linear and branched alkanes to be fed to the steam cracker and another stream, for example containing cycloalkanes and/or cycloalkenes, to be recycled to the catalytic cracker of the process according to the invention.

If the reaction product still contains unreacted $C_5$ and/or $C_6$ cycloalkanes, the reaction product is preferably separated into at least one fraction containing propylene and one fraction containing unconverted $C_5$ and/or $C_6$ cycloalkanes; followed by recycling at least part of the unconverted $C_5$ and/or $C_6$ cycloalkanes.

The present invention therefore also provides a process for the preparation of propylene from a hydrocarbon feed containing one or more $C_5$ and/or $C_6$ cycloalkanes, comprising the steps of
a) contacting the hydrocarbon feed containing one or more $C_5$ and/or $C_6$ cycloalkanes under cracking conditions with a zeolite catalyst as described hereinbefore to yield a reaction product containing propylene and unconverted $C_5$ and/or $C_6$ cycloalkanes;
b) separating at least part of the unconverted $C_5$ and/or $C_6$ cycloalkanes from the reaction mixture and recycling the separated unconverted $C_5$ and/or $C_6$ cycloalkanes to step a).

Preferably more than 50% w/w, more preferably more than 70% w/w, even more preferably more than 90% w/w and most preferably all (about 100% w/w) of the unconverted $C_5$ and/or $C_6$ cycloalkanes is recycled.

The reaction product of the process of the invention can be further processed in several ways.

In a further embodiment, if a partly hydrogenated feed is used in the process, the reaction product can still contain unconverted $C_5$ and/or $C_6$ cycloalkenes. If such unconverted $C_5$ and/or $C_6$ cycloalkenes are present, these are preferably hydrogenated and subsequently recycled. More preferably such $C_5$ and/or $C_6$ unsaturated cyclic hydrocarbons are fully hydrogenated before being recycled.

The present invention therefore also provides a process for the preparation of propylene from a hydrocarbon feed containing one or more $C_5$ and/or $C_6$ cycloalkanes and one or more $C_5$ and/or $C_6$ cycloalkenes, comprising the steps of
a') contacting the hydrocarbon feed under cracking conditions with a one-dimensional zeolite having a 10 membered ring and a Silica to Alumina ratio in the range from 1 to 500 to yield a reaction product containing propylene, unconverted $C_5$ and/or $C_6$ cycloalkenes or cycloalkadienes, and optionally unconverted $C_5$ and/or $C_6$ cycloalkanes;
b') separating the reaction mixture of step a') in at least one fraction containing propylene and at least one fraction containing unconverted $C_5$ and/or $C_6$ cycloalkenes or cycloalkadienes, and optionally unconverted $C_5$ and/or $C_6$ cycloalkanes;
c') partly or fully hydrogenating the fraction containing unconverted $C_5$ and/or $C_6$ cycloalkenes or cycloalkadienes obtained in step b') to yield a stream containing $C_5$ and/or $C_6$ cycloalkanes; and
d') recycling the stream of $C_5$ and/or $C_6$ cycloalkanes obtained in step c') to step a').

Preferably more than 50% w/w, more preferably more than 70% w/w, even more preferably more than 90% w/w and most preferably all (about 100% w/w) of the unconverted $C_5$ and/or $C_6$ cycloalkenes and optionally unconverted $C_5$ and/or $C_6$ cycloalkanes is hydrogenated and recycled. The hydrogenating of step c') can be carried out as described hereinbefore. Preferably the unconverted $C_5$ and/or $C_6$ cycloalkenes in step c') are fully hydrogenated.

The reaction product of the process according to the invention can further contain $C_5$ and/or $C_6$ normal- and/or iso-alkanes. In a further preferred embodiment such $C_5$ and/or $C_6$ normal- and/or iso-alkanes are separated and preferably subsequently fed to a steam cracker. Accordingly the present invention also provides a process for the preparation of propylene from a hydrocarbon feed containing one or more $C_5$ and/or $C_6$ cycloalkanes; one or more $C_5$ and/or $C_6$ normal- and/or iso-alkanes and optionally one or more $C_5$ and/or $C_6$ cycloalkenes and/or cycloalkadienes, comprising the steps of:
a") contacting the hydrocarbon feed with a one-dimensional zeolite having a 10 membered ring and a Silica to Alumina ratio in the range from 1 to 500, yielding a reaction mixture containing propylene and $C_5$ and/or $C_6$ hydrocarbons;
b") separating the reaction mixture of step a") in at least one fraction containing propylene and at least one fraction containing $C_5$ and/or $C_6$ hydrocarbons;
c") optionally partly or fully hydrogenating the fraction containing $C_5$ and/or $C_6$ hydrocarbons obtained in step b") to yield a stream of partly or fully hydrogenated $C_5$ and/or $C_6$ hydrocarbons;
d") separating the obtained $C_5$ and/or $C_6$ hydrocarbons of step b") or c") into at least one fraction containing $C_5$ and/or $C_6$ normal- and/or iso-alkanes and at least one fraction containing $C_5$/$C_6$ cyclic hydrocarbons;
e") recycling the stream of $C_5$ and/or $C_6$ cyclic hydrocarbons obtained in step d") to step a");
f") feeding the fraction containing $C_5$ and/or $C_6$ normal- and/or iso-alkanes obtained in step d") to a thermal cracker.

The process according to the invention, wherein optionally also one or more hydrogenation steps are included, can be carried out in several industrial set-ups. Some of such industrial set-ups are also considered to be novel. Therefore the present invention further provides an industrial set-up for converting a hydrocarbon feed to propylene containing a first hydrogenation unit of which at least one outlet is connected to the inlet of a catalytic cracker unit, which catalytic cracker unit in operation contains a one-dimensional zeolite having a 10 membered ring and a Silica to Alumina ratio in the range from 1 to 500. Preferably at least one of the outlets of the catalytic cracker unit is connected to the inlet of a separating unit, where the product stream of the catalytic cracker unit can be separated into a propylene containing stream and a stream containing $C_{4+}$ hydrocarbons. The stream containing $C_{4+}$ hydrocarbons can be led into a steam cracker unit; or can be recycled, optionally via a second hydrogenation unit, to the catalytic cracker unit. In a further embodiment the stream containing $C_{4+}$ hydrocarbons can be led into a second hydrogenation unit for full hydrogenation and subsequently be led into a further (second) separation unit. In such a further (second) separation unit, the stream containing $C_{4+}$ hydrocarbons can be separated into a stream containing cyclic $C_{4+}$ hydrocarbons and a stream containing linear and branched $C_{4+}$ hydrocarbons. The stream containing cyclic $C_{4+}$ hydrocarbons can be recycled to the catalytic cracker unit. The stream containing linear and branched $C_{4+}$ hydrocarbons is preferably led into a steam cracker unit.

Such an industrial set-up and process has been illustrated in FIG. 1. In FIG. 1 a stream of hydrocarbon feed (1) containing one or more $C_5$ and/or $C_6$ cycloalkanes and one or more $C_5$ and/or $C_6$ cycloalkenes is fed to a hydrogenation unit (2), where it is contacted with a stream of hydrogen (3). The (partially) hydrogenated product stream (4) of the hydrogenation unit (2) is fed into a catalytic cracker unit (5), where it is contacted with a one-dimensional zeolite having a 10 membered ring and a silica to alumina ratio in the range from 1 to 500. The product stream (6) of this cracker unit (5) can be separated in a separating unit (7) into a propylene containing stream (8) and a stream containing unconverted $C_5$ and/or $C_6$ cycloalkanes, and optionally unconverted $C_5$ and/or $C_6$ cycloalkenes (9). Such stream (9) can be recycled to the catalytic cracker unit (5), optionally via a second hydrogenation unit (10).

Figure 2:
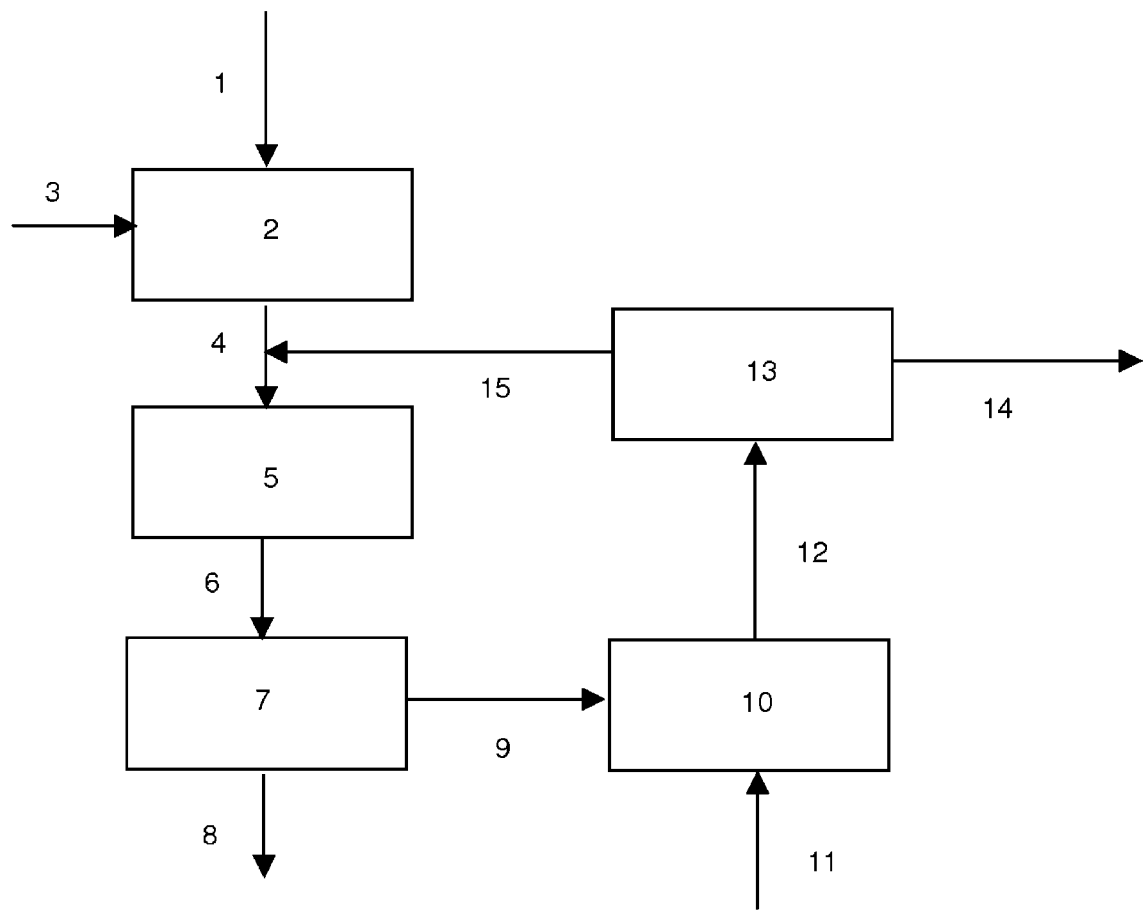

A further industrial set-up and process have been illustrated in FIG. 2. In FIG. 2 the set-up and process is as illustrated in FIG. 1, except that the stream (9) is fed into a second hydrogenation unit (10) where it is contacted with a further hydrogen stream (11). The hydrogenated product stream (12) of this second hydrogenation unit (10) can subsequently be separated in a second separating unit (13) into a stream containing non-cyclic hydrocarbons (14) and a stream containing cyclic hydrocarbons (15). Such stream (15) can be recycled to the cracking unit (5).

In a preferred embodiment the hydrocarbon steam (1) in FIGS. 1 and/or 2 is fully or partly generated in a distillation unit (16, not shown) that is connected to a steam cracker (17, not shown).

In a further preferred embodiment the hydrocarbon stream (1) in FIGS. 1 and/or 2 is fully or partly generated in a distillation unit (18, not shown) that is connected to a benzene extraction unit (19, not shown).

Figure 3:
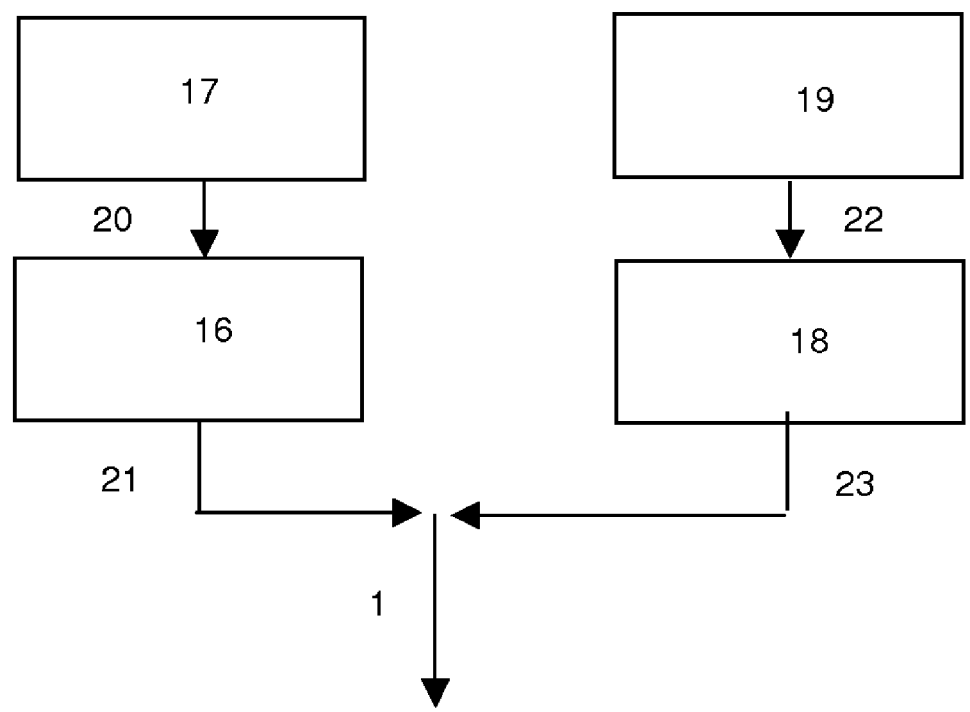

A further industrial set-up and process have been illustrated in FIG. 3. In FIG. 3 the set-up and process is as illustrated in FIG. 1, except that the hydrocarbon stream (1) is partly obtained from a distillation unit (16) that is connected to a steam cracker (17) and partly from a distillation unit (18) that is connected to a benzene extraction unit (19).

The invention will hereinbelow be further illustrated by the following non-limiting examples.

EXAMPLE 1

In this example cyclopentane was reacted over a MFI type zeolite catalyst with a silica to alumina ratio of 280 (comparative) and a MTT type zeolite catalyst with a silica to alumina ratio of 48 (according to the invention). A sample of zeolite powder was pressed into tablets and the tablets were broken into pieces and sieved. For catalytic testing, the sieve fraction of 30-80 mesh has been used. A quartz reactor tube of 3 mm internal diameter was loaded with 400 mg of sieve fraction. Prior to reaction, the fresh catalyst in its ammonium-form was treated with flowing argon at 550° C. for 1 hour. Next, the catalyst was cooled in argon to the reaction temperature and a mixture consisting of 2.1 vol. % cyclopentane (CP) and 1 vol. % of water (in argon) was passed over the catalyst at atmospheric pressure (1 bar) at a flow rate of 50 ml/minute. Periodically, the effluent from the reactor was analyzed by gas chromatography (GC) to determine the product composition. The composition has been calculated on a weight basis of the total effluent of the reactor. As can be seen the process of the present invention results in a high yield of propylene and little co-production of undesirable butene-byproducts. Another valuable product produced is ethylene.

The following table lists the reaction parameters together with the product composition, as determined by GC:

TABLE 1

Conversion of cyclopentane

| Zeolite | MTT | MFI* | MTT | MFI* |
|---|---|---|---|---|
| Time on stream, hours | 9 | 8 | 29 | 28 |
| Temperature, ° C. | 500° C. | 500° C. | 500° C. | 500° C. |
| CP conversion, wt % | 72.6 | 51.6 | 65.9 | 53.2 |
| Ethylene, wt. % | 23.9 | 12.6 | 20.7 | 13.8 |
| Propylene, wt. % | 34.1 | 19.4 | 30.0 | 20.8 |
| Butene isomers, wt. % | 3.1 | 5.9 | 2.4 | 6.7 |
| Hexene isomers, wt. % | 1.8 | 1.5 | 1.4 | 1.4 |
| Propylene to Butene weight ratio | 11 | 3.3 | 12.5 | 4.8 |

*= comparative

EXAMPLE 2

In this example methyl-cyclopentane was reacted over over a MFI type zeolite catalyst with a silica to alumina ratio of 280 (comparative) and a MTT type zeolite catalyst with a silica to alumina ratio of 48 (according to the invention). A sample of zeolite powder was pressed into tablets and the tablets were broken into pieces and sieved. For catalytic testing, the sieve fraction of 30-80 mesh has been used. A quartz reactor tube of 3 mm internal diameter was loaded with 200 mg of sieve fraction. Prior to reaction, the fresh catalyst in its ammonium-form was treated with flowing argon at 550° C. for 1 hour. Next, the catalyst was cooled in argon to the reaction temperature and a mixture consisting of 1.2 vol. % methyl-cyclopentane (MCP) and 1 vol. % of water (in argon) was passed over the catalyst at atmospheric pressure at a flow rate of 50 ml/minute. Periodically, the effluent from the reactor was analyzed by gas chromatography (GC) to determine the product composition. The composition has been calculated on a weight basis of the total effluent of the reactor.

As can be seen the process of the present invention results in a high selectivity to propylene and little co-production of undesirable butene-byproducts. Another valuable product produced is ethylene.

The following table (table 2) lists the reaction parameters together with the product composition, as determined by GC:

TABLE 2

Conversion of methyl-cyclopentane

| Zeolite | MTT | MFI* | MTT | MFI* |
|---|---|---|---|---|
| Time on stream, hours | 8.5 | 8 | 10 | 9.5 |
| Temperature ° C. | 550° C. | 550° C. | 550° C. | 550° C. |
| MCP conversion, wt % | 41.9 | 72.6 | 41.0 | 72.2 |
| Ethylene, wt. % | 2.0 | 5.2 | 1.9 | 5.0 |
| Propylene, wt. % | 37.0 | 55.4 | 35.5 | 53.4 |
| Butene isomers, wt. % | 2.3 | 8.1 | 2.1 | 8.0 |
| Hexene isomers, wt. % | 3.2 | 5.0 | 2.9 | 4.8 |
| Propylene to Butene weight ratio | 16.1 | 6.8 | 16.9 | 6.7 |

*= comparative

EXAMPLE 3

In this example a sample consisting of semi-hydrotreated $C_5$ pyrolysis gasoline (pygas) was reacted over a MFI zeolite (comparative) and a MTT zeolite (according to the invention). The silica-to-alumina ratio were 280 and 48 for MFI and MTT, respectively.

The C$_5$ pyrolysis gasoline contained C$_4$ alkenes (about 5 vol. %), linear and branched C$_5$ alkanes (about 30 vol. %), linear and branched C$_5$ alkenes (about-50 vol. %), cyclopentane (about 5 vol. %), cyclopentene (about 8 vol. %), benzene (about 0.5-1 vol. %) and small amounts (less than 0.2 vol. %) of various components, such as, pentadienes and cyclopentadiene.

A sample of zeolite powder was pressed into tablets and the tablets were broken into pieces and sieved. For catalytic testing, the sieve fraction of 30-80 mesh has been used. A quartz reactor tube of 3 mm internal diameter was loaded with 200 mg of sieve fraction. Prior to reaction, the fresh catalyst in its ammonium-form was treated with flowing argon at 550° C. for 1 hour. Next, the catalyst was cooled in argon to the reaction temperature and a mixture consisting of about 3 vol. % pyrolysis gasoline and 1 vol. % of water (in argon) was passed over the catalyst at atmospheric pressure (1 bar) at a flow rate of 50 ml/minute. Periodically, the effluent from the reactor was analyzed by gas chromato-graphy (GC) to determine the product composition. The composition has been calculated on a weight basis. The selectivity is calculated by dividing the mass of the specific product by the sum of the masses of the total of products, excluding any unreacted feed.

The following table (table 3) lists some of most important reaction parameters together with the compositional data, as determined by GC:

TABLE 3

|  | MTT | MFI* |
|---|---|---|
| Temperature ° C. | 525° C. | 525° C. |
| Total C$_5$ conversion, wt % | 40 | 60 |
| Cyclopentane conversion, wt % | 30 | 75 |
| Ethylene selectivity, wt % | 34 | 32 |
| Propylene selectivity, wt % | 51 | 49 |
| Butene isomers selectivity, wt % | 5 | 9 |
| C$_6$/C$_7$ isomers selectivity, wt % | 8 | 10 |
| Propylene to Butene weight ratio | 10.2 | 5.4 |

*= comparative

What is claimed is:

1. A process for the preparation of propylene from a hydrocarbon feed containing at least 1% w/w of one or more C$_5$ and/or C$_6$ cycloalkanes, wherein the hydrocarbon feed containing one or more C$_5$ and/or C$_6$ cycloalkanes is contacted under cracking conditions with a one-dimensional zeolite having 10-membered ring channels and a silica to alumina ratio in the range from 1 to 500 so as to convert the C$_5$ and/or C$_6$ cycloalkanes to yield propylene, and wherein at least 50% w/w of the total amount of zeolite used is zeolite in the hydrogen form.

2. The process according to claim 1, wherein the hydrocarbon feed containing one or more C$_5$ and/or C$_6$ cycloalkanes is contacted under cracking conditions with the zeolite in the absence of any metals belonging to Group Ib of the periodic table.

3. The process according to claim 1, wherein the hydrocarbon feed containing one or more C$_5$ and/or C$_6$ cycloalkanes is obtained by full or partial hydrogenation of a hydrocarbon feed containing one or more C$_5$ and/or C$_6$ unsaturated cyclic hydrocarbons.

4. The process according to claim 1, wherein the hydrocarbon feed comprises an, optionally hydrogenated, C$_5$ and/or C$_6$ stream derived from pyrolysis gasoline that is produced in a steam cracker.

5. The process according to claim 1, wherein the zeolite is chosen from the group consisting of TON-type, MTT-type, SFF-type, STF-type, EUO-type, and EU-2-type zeolites.

6. The process according to claim 1, wherein the zeolite is a MTT-type zeolite.

7. The process according to claim 1, wherein the zeolite has a silica to alumina ratio in the range from 10 to 200.

8. The process according to claim 1, wherein hydrocarbon feed is contacted with the zeolite at a temperature in the range from 300° C. to 700° C., and at an absolute pressure in the range from 1 to 5 bar.

9. The process according to claim 1, wherein the process is carried out in the absence of oxygenates.

10. The process according to claim 1, wherein at least part of any unconverted feed is recycled.

* * * * *